| United States Patent [19] | [11] Patent Number: 4,536,307 |
| Horodysky | [45] Date of Patent: Aug. 20, 1985 |

[54] LUBRICANT COMPOSITION

[75] Inventor: Andrew G. Horodysky, Cherry Hill, N.J.

[73] Assignee: Mobil Oil Corporation, New York, N.Y.

[21] Appl. No.: 535,139

[22] Filed: Sep. 23, 1983

[51] Int. Cl.³ .............................................. C10M 1/36
[52] U.S. Cl. ........................... 252/32.7 E; 252/51.5 A; 252/392; 252/389.41; 252/389 R; 564/8
[58] Field of Search ..................... 252/32.7 E, 51.5 A, 252/392, 389.41; 564/8

[56] References Cited

U.S. PATENT DOCUMENTS 2,935,389  5/1960  Tilsworth et al. ................. 252/392
3,109,719  11/1963  Eckert ............................... 252/392
4,052,322  10/1977  Crookshank ....................... 252/40
4,474,671  10/1984  Herd et al. ...................... 252/33.6

*Primary Examiner*—Jacqueline V. Howard
*Attorney, Agent, or Firm*—Alexander J. McKillop; Michael G. Gilman; Claude E. Setliff

[57] ABSTRACT

Borated acyl sarcosines have been found to be effective multifunctional additives when added to lubricating oils or greases therefrom. They can be used as antirust, antifriction or anticorrosion agents.

31 Claims, No Drawings

LUBRICANT COMPOSITION

BACKGROUND OF THE INVENTION

1. Field of the Invention

This invention relates to a multifunctional additive which, when added to a lubricant or fuel, will reduce friction and inhibit rust and corrosion associated with same. More particularly, the invention relates to lubricants to which has been added an antifriction, antirust or anticorrosion amount of a borated acyl sarcosine.

2. Discussion of the Prior Practices

It is well known that, under certain conditions, metal parts being lubricated will rust. That is to say, when certain types of materials that are normally susceptible to deterioration by oxidation or by corrosion come into contact with various organic media, rust may form. Organic compositions in both the liquid and solid form can induce such corrosion or oxidation. For example, it is known that liquid hydrocarbons in the form of various fuel oils, such as petroleum distillate hydrocarbon fuels, lubricating oils, or greases therefrom, tend to accumulate considerable quantities of water when maintained for long periods of time in storage vessels; and when subsequently brought into contact with metal surfaces in their functional environments, deterioration of said surfaces as a result of rust and corrosion occurs. In addition, where such lubricating oils are incorporated into lubricants in the form of greases, similar deleterious results are encountered.

No art is known that teaches or suggests the reaction product of the present compositions. It is well known that amines and other nitrogen-containing compounds have been used as antioxidants. For example, N-phenylalpha-naphthylamine has been used alone and in combination with other materials as an antioxidant.

Many varied borated amides, borated alkanolamines, borated ureas, amine salts or boron acids, chlorinated amine-boron complexes and aromatic amine-boron mixtures have been used in the past in commercial lubricant and fuel applications as described in U.S. Pat. Nos. 3,449,362, 3,354,025, 2,999,064, 4,226,734, 3,076,835, 4,025,445, 3,014,870, 3,014,869 and 3,007,873. In fact, alkylamines, alkyldiamines and borated adducts of alkylamines and diamines have been used as friction reducing additives in lubricants as described in U.S. Pat. No. 4,328,113. The borated acyl sarcosines described here provide advantages in antirust, friction reducing, oxidative and high temperature stability performance properties unavailable in any of the prior art statements. The additive compositions, as well as the lubricant and fuel compositions made therewith are believed to be novel, and are not believed to be described in any reference. The closest reference applicants are aware of is U.S. Pat. No. 4,195,977, directed to etherdiamine salts of an N-acyl sarcosine and liquid hydrocarbons containing same.

SUMMARY OF THE INVENTION

In accordance with the invention, there is provided a lubricant or liquid fuel composition comprising a major proportion of a lubricant or fuel and antifriction, antirust or anticorrosion amount of a product of reaction made by reacting (1) a boron-containing compound with (2) an acyl sarcosine of the formula:

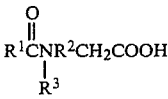

where $R^1$ is a hydrocarbyl group, preferably an alkyl group, containing 1 to 20 carbon atoms including methyl, propyl, hexyl, octyl, tetradecyl, octadecyl and eicosyl, $R^2$ is a hydrocarbylene group containing 1 to 6 carbon atoms, preferably methylene, but can also be ethylene, propylene, butylene, amylene or hexylene and $R^3$ is hydrogen or a hydrocarbyl group containing 1 to 6 carbon atoms. $R^3$ is preferably a methyl, ethyl, propyl, isopropyl, butyl, amyl or hexyl group. Hydrocarbyl (as used in "hydrocarboxy" etc.) includes alkyl, alkenyl, cycloalkyl, cycloalkenyl, alkaryl, aralkyl, and the like, and mixtures of these In addition, the invention provides the product of reaction.

DESCRIPTION OF SPECIFIC EMBODIMENTS

Borated sarcosines demonstrate exceptional antirust, antioxidant and friction reducing properties when formulated into lubricants or liquid fuels at low additive concentrations. The acyl sarcosines are generally available from commercial sources. However, in general they can be made by reacting the appropriate amino acid with the appropriate acyl chloride, preferably the halide. The borated sarcosines can in turn be synthesized by the boration of the acyl sarcosine.

The boron compound can be any compound capable of use as a borating agent. Preferred are boron oxide and a boron compound of the formula:

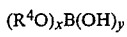

wherein $R^4$ is a $C_1$ to $C_6$ alkyl group, x is 0 to 3 and y is 0 to 3, the sum of x and y being 3. Included within the formula are boric acid and alkyl borates, such as the mono-, di- and trimethyl borates, the mono-, di- and triethyl borates, the mono-, di- and tributy borates and the mono-, di- and trihexyl borates. Some of the other borates include metaborates and aryl borates.

The acyl sarcosines useful in practicing the invention include lauroyl sarcosine, tridecoyl sarcosine, hexadecoyl sarcosine, heptadecoyl sarcosine, oleoyl sarcosine, soyoyl sarcosine, hydrogenated tallowoyl sarcosine, halogenated linolenyl sarcosine, tallowoyl sarcosine, cocyl sarcosine and decoyl sarcosine.

The reaction of the sarcosine with the boron compound may be carried out at from about 80° C. to about 260° C., preferably from 120°–180° C. Times of reaction are not critical. Thus, although we do not wish to be confined to any time limitation, we contemplate that the products of this invention can be made by carrying out the reaction for from 1 to 20 hours.

Solvents are preferred in carrying out the invention. Broadly, any solvent can be used that does not react, is a solvent for both the reactants and the reaction product and can be removed easily or is compatible with the environment in which the product will be used. We prefer the hydrocarbon solvents such as toluene, benzene, and xylenes for either reaction. Low molecular weight alcohols such as butanol or hexamethyl glycol can be used for the boration reaction in addition or in place of hydrocarbon solvents.

A specific level of boration is not critical to obtain maximum benefits. The level of boron in the final product should be at least 0.02%, but could be up to 10% or more by weight. A preferred boron content is often 0.1% to 4%. These borated compounds are used with lubricating oils and lubricating greases to the extent of from about 0.1% to about 10% by weight of the total composition.

The borated sarcosine-lubricant compositions can include other additives, such as detergents, antioxidants, antiwear agents, viscosity index improvers, pour depressants, dispersants and the like. These specifically include phenates, sulfonates, succinimides, the nickel, cadmium and zinc dithiophosphates, the ashless dithiophosphates, such as those containing the vinyl ether, the vinyl ester or the epoxide moiety. These dithioate additives may be present at concentrations of from about 0.1% to about 5% by weight of the composition, preferably about 0.25% to about 2% by weight.

An important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle. In general, mineral oils, both paraffinic, naphthenic and mixtures thereof, employed as a lubricating oil or as the grease vehicle, may be of any suitable lubricating viscosity range, as for example, from about 45 SSR at 100° F. to about 6000 SSU at 100° F., and preferably from about 50 to about 250 SSR at 210° F. These oils may have viscosity indexes ranging to about 100 or higher. Viscosity indexes from about 70 to 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, including calcium or lithium soaps, which are dispersed in the lubricating vehicle in grease-forming quantities in an amount to impart to the resulting grease composition the desired consistency. Other thickening agents that may be employed in the soap thickeners can include calcium or lithium stearates or calcium or lithium hydroxy stearates. Included are greases thickened by the use of at least a portion of metallic hydroxystearate thickener, which can be made of the conventional reaction of lithium hydroxide with 12-hydroxystearic acid, or the corresponding methyl esters or glycerides. The grease formulation may also comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned grease in accordance with the present invention.

In instances where synthetic oils, are to be used per se or as the vehicle for the grease, various synthetic oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether, phenoxy phenylethers.

It is to be understood that the compositions contemplated herein may also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl or diaryl dithiophosphates, and the like. These materials do not detract from the value of the compositions of this invention; rather the materials serve to impart their customary properties to the particular compositions in which thay are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2; RR 1005 on "Automatic Transmission Fluid/Power Transmission Fluid Property and Performance Definitions. Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the reaction products of the present invention may be employed in a lubricant in any amount which is effective for imparting the desired degree of antirust activity, antioxidant or friction reduction activity. In these applications, the product is effectively employed in amounts from about 0.1% to about 10% by weight, and preferably from about 1% to about 5% of the total weight of the composition.

The following Examples will illustrate the invention. It will be understood that they are illustrative only and it is not intended that the invention shall be limited thereof.

EXAMPLE 1

Approximately 175 g of oleoyl sarcosine (obtained commercially as Hamposyl O from W. R. Grace & Co.), 75 g of toluene and 10 g of boric acid were added to a 1 liter glass reactor fitted with heater, agitator, Dean-Stark tube and condenser, and provision to blanket the vapor space with nitrogen. The reaction mixture was heated up to 150° C. for 4 hours until water evolution during solvent azeotroping ceased. The solvent was removed by vacuum distillation at about 150° C. and the

EXAMPLE 2

Borated Oleoyl Sarcosine

Approximately 115 g of oleoyl sarcosine (obtained commercially as Hamposyl O from W. R. Grace & Co.), 75 g of toluene and 75 g of boric acid were charged to a reactor equipped as described in Example 1. The reaction mixture was heated up to 160° C. for 4 hours until water evolution during azeotropic distillation stopped. The solvent was removed by vacuum distillation at about 160° C. and the product was cooled to 100° C. and filtered through diatomaceous earth.

EXAMPLE 3

Borated Oleoyl Sarcosine

Approximately 175 g of oleoyl sarcosine (obtained commercially as Hamposly O from W. R. Grace & Co.), 75 g of toluene and 15 g of boric acid were charged to a reactor equipped as described in Example 1. The reaction mixture was heated up to 150° C. for 3 hours until water evolution during azeotropic distillation stopped. Approximately 7½ g water was collected. The solvent was removed by vacuum distillation at about 150° C. and the product was cooled to about 100° C. and filtered through diatomaceous earth.

EXAMPLE 4

Borated Cocoyl Sarcosine

Approximately 140 g of cocoyl sarcosine (obtained commercially as Hamposyl C from W. R. Grace & Co.), 100 g of toluene and 10 g of boric acid were added to a 1 liter glass reactor equipped as described in Example 1. The reaction mixture was heated up to 160° C. for 4 hours until water evolution stopped. The solvent was removed by vacuum distillation at about 160° C.; the product was cooled to 120° C. and filtered through diatomaceous earth.

EXAMPLE 5

Borated Lauroyl Sarcosine

Approximately 175 g of lauroyl sarcosine (obtained commercially as Hamposyl L from W. R. Grace & Co.), 100 g of toluene and 12 g of boric acid were charged to a reactor equipped as described in Example 1. The reaction mixture was heated up to 160° C. for 3 hours and held until water evolution during axeotropic distillation ceased. The solvent was removed by vacuum distillation at 160° C. The product was cooled to about 120° C. and filtered through diatomaceous earth.

EVALUATION OF THE COMPOUNDS

The borated acyl sarcosines were blended into several lubricating fluids and evaluated for friction reducing properties as shown in Tables 1 and 2. Each of the products exhibit significant friction reducing properties with reductions in the coefficients of friction as high as 53%.

The compounds were evaluated in a Low Velocity Friction Apparatus (LVFA) in a fully formulated mineral or synthetic, automotive engine oil containing an additive package including zinc dithiophosphate, antioxidant, dispersant and detergent.

DESCRIPTION

The Low Velocity Friction Apparatus (LVFA) is used to measure the coefficient of friction of test lubricants under various loads, temperatures, and sliding speeds. The LVFA consists of a flat SAE 1020 steel surface (diameter 1.5 in.) which is attached to a drive shaft and rotated over a stationary, raised, narrow ringer SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y-axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever cam-motor arrangement.

Procedure

The rubbing surfaces and 12–13 ml of test lubricants are placed on the LVFA. A 240 psi load is applied and the sliding speed is maintained at 40 fpm at ambient temperature for a few minutes. A plot for coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

Frictional Properties
Low Velocity Friction Apparatus Test

|  | Conc. in Base Oil, Wt. % | % Reduction in Coefficient of Friction | |
| --- | --- | --- | --- |
|  |  | 5 Ft./Min. | 30 Ft./Min. |
| Base Oil - 10W-40 fully formulated engine oil containing detergent/dispersant/inhibitor package | — | 0 | 0 |
| Example 1 Plus Base Oil | 2 | 32 | 20 |
|  | 1 | 29 | 13 |
| Example 2 Plus Base Oil | 2 | 48 | 32 |
| Example 4 Plus Base Oil | 2 | 52 | 37 |
|  | 1 | 38 | 21 |
| Example 5 Plus Base Oil | 2 | 53 | 36 |
|  | 1 | 30 | 16 |

TABLE 2

Frictional Properties
Low Velocity Friction Apparatus Test

|  | Conc. in Base Oil, Wt. % | % Reduction in Coefficient of Friction | |
| --- | --- | --- | --- |
|  |  | 5 Ft./Min. | 30 Ft./Min. |
| Base Oil - 5W-30 fully | — | 0 | 0 |

TABLE 2-continued

Frictional Properties
Low Velocity Friction Apparatus Test

|  | Conc. in Base Oil, Wt. % | % Reduction in Coefficient of Friction | |
|---|---|---|---|
|  |  | 5 Ft./Min. | 30 Ft./Min. |
| formulated synthetic engine oil containing detergent/dispersant/inhibitor package |  |  |  |
| Example 1 Plus Base Oil | 2 | 44 | 31 |
|  | 1 | 26 | 17 |
| Example 2 Plus Base Oil | 2 | 48 | 32 |
| Example 4 Plus Base Oil | 2 | 25 | 27 |
| Example 5 Plus Base Oil | 2 | 25 | 27 |
|  | 1 | 18 | 14 |

The oxidative performance properties were measured using the Catalytic Oxidation Test at 325° F. for 40 hours. In this test air is bubbled into the test solution containing samples of metals of construction, e.g., lead and copper, for the time and at the temperature taught. As shown by the test results, the borated acyl sarcosines, in general, had a beneficial effect upon controlling both viscosity increase and generation of acidity.

TABLE 3

Catalytic Oxidation Test
40 Hrs. @ 325° F.

|  | Concentration in Base Oil, % | Percent Visc. Increase When Measured @ 100° C., % | Number |
|---|---|---|---|
| Base Oil - 200" solvent paraffinic neutral lubricating oil | — | 0 | 0 |
| Example 1 Plus Base Oil | 2 | 16 | 1.98 |
|  | 1 | 17 | 2.20 |
| Example 2 Plus Base Oil | 1 | 22 | 6.05 |
| Example 3 Plus Base Oil | 2 | 16 | 1.93 |
|  | 1 | 17 | 2.53 |

The product of Example 1 was formulated at the 1 wt. % and ½ wt. % level into a fully formulated lithium 12-hydroxystearate soap grease without any other added antirust additive. Included was approximately 1½% of a zinc dialkl dithiophosphate derived from primary and secondary butanols and pentanols. A standard test method (ASTM D1743) for corrosion prevention properties of lubricating grease was used. This method covers determination of the corrosion preventive properties of greases using grease-lubricated tapered roller bearings stored under wet conditions. After cleaning, the bearing cup raceways were examined for evidence of corrosion. As can be seen from the test results, the product of this developemnt provides substantial protection against corrosion.

TABLE 4

ASTM D1743 Grease Rust Test

| | Concentration in Lithium Soap Grease fully Formulated but Without Rust Inhibitor, % | Rust Test Result |
|---|---|---|
| Example 1 | 1 | 1,1,1 |
|  | 0.5 | 1,1,3 |

A rust test result of 1 indicates no rust.

We claim:

1. A product of reaction made by reacting a boron compound with an acyl sarcosine of the formula

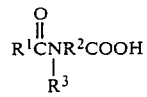

wherein $R^1$ is a hydrocarbyl group containing 1 to 20 carbon atoms, $R^2$ is a $C_1$ to $C_6$ hydrocarbylene group and $R^3$ is hydrogen or a $C_1$ to $C_6$ hydrocarbyl group, the reaction being carried out at from about 80°C. to about 260° c. using sufficient reactants to provide from about 0.02% to about 10% by weight of boron in the final product wherein the boron compound is boron oxide or has the formula

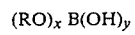

wherein R is a $C_1$ to $C_6$ alkyl group, x is 0 to 3 and y is 0 to 3, the sum of x and y being 3.

2. The product of claim 1 wherein the boron compound is boric acid.

3. The product of cliam 1 wherein the hydrocarbyl groups are selected from the group consisting of alkyl, alkenyl, cycloalky, cycloalkenyl, alkaryl, aralkyl and mixtures thereof.

4. The product of claim 3 wherein $R^1$ is an alkyl group.

5. The product of claim 3 wherein $R^3$ is an alkyl group.

6. The product of claim 1 wherein $R^2$ si a methylene group.

7. The product of claim 1 wherein the acyl sarcosine is oleoyl sarcosine and the boron compound is boric acid.

8. The product of claim 1 wherein the acyl sarcosine is cocoyl sarcosine and the boron compound is boric acid.

9. The product of claim wherein the acyl sarcosine is lauroyl sarcosine and the boron compound is boric acid.

10. A lubricant composition comprising a major proportion of a lubricating oil or grease therefrom and a friction reducing amount of a reaction product made by reacting a boron compound with an acyl sarcosine of the formula

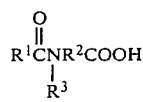

wherein $R^1$ is a hydrocarbyl group containing 1 to 20 carbon atoms, $R^2$ is a $C_1$ to $C_6$ hydrocarbylene group and $R^3$ is hydrogen or a $C_1$ to $C_6$ hydrocarbyl group, the reaction being carried out at from about 80° C. to about 260° C. using sufficient reactants to provide from about 0.02% to about 10% by weight of boron in the final product.

11. The composition of claim 10 wherein the boron compound is boron oxide or has the formula

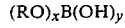

wherein R is a $C_1$ to $C_6$ alkyl group, x is 0 to 3 and y is 0 to 3, the sum of x and y being 3.

12. The composition of claim 11 wherein the boron compound is boric acid.

13. The composition of claim 10 wherein the hydrocarbyl groups are selected from the group consisting of alkyl, alkenyl, cycloalkyl, cycloalkenyl, alkaryl, aralkyl and mixture thereof.

14. The composition of claim 13, wherein $R^1$ is an alkyl group.

15. The composition of claim 13 wherein $R^3$ is an alkyl group.

16. The composition of claim 10 wherein $R^2$ is an methylene group.

17. The composition of claim 10 wherein the acyl sarcosine is oleoyl sarcosine and the boron compound is boric acid.

18. The composition of claim 10 wherein the acyl sarcosine is cocoyl sarcosine and the boron compound is boric acid.

19. The composition of claim 10 wherein the acyl sarcosine is lauroyl sarcosine and the boron compound is boric acid.

20. The composition of claim 10 wherein the lubricant is (1) a mineral oil, (2) a synthetic oil or mixture of synthetic oils, (3) a mixture of (1) and (2) or a grease from (1), (2) or (3).

21. The composition of claim 20 wherein the lubricant is the mineral oil of (1).

22. The composition of claim 20 wherein the lubricant is the synthetic oil of (2).

23. The composition of claim 20 wherein the lubricant is the mixture of synthetic oils of (2).

24. The composition of claim 20 wherein the lubricant is a mixture of the mineral oil of (1) and the synthetic oil or mixtures thereof of (2).

25. The composition of claim 20 wherein the lubricant is a grease of (1), (2) or (3).

26. The composition of claim 25 wherein the grease is prepared from mineral oil.

27. The composition of claim 26 wherein the grease is thickened with a hydroxy stearate.

28. The composition of claim 27 wherein the hydroxy stearate is lithium 12-hydroxy stearate.

29. The composition of claim 28 additionally comprising from about 0.1% to about 5% by weight of a metal dialkyl phosphorodithioate.

30. The composition of claim 29 wherein the metal is zinc.

31. A method of decreasing fuel consumption in an internal combustion engine which comprises lubricating said engine with a lubricant composition comprising a major proportion of a lubricating oil and a fuel reducing amount of a product of reaction made by reacting a boron compound with an acyl sarcosine of the formula

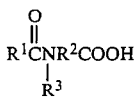

wherein $R^1$ is a hydrocarbyl group containing 1 to 20 carbon atoms, $R^2$ is a $C_1$ to $C_6$ hydrocarbylene group and $R^3$ is hydrogen or a $C_1$ to $C_6$ hydrocarbyl group, the reaction being carried out at from about 80° C. to about 260° C. using sufficient reactants to provide from about 0.02% to about 10% by weight of boron in the final product.

* * * * *

UNITED STATES PATENT AND TRADEMARK OFFICE
CERTIFICATE OF CORRECTION

PATENT NO. : 4,536,307
DATED : August 20, 1985
INVENTOR(S) : Andrew G. HORODYSKY It is certified that error appears in the above-identified patent and that said Letters Patent is hereby corrected as shown below:

Col. 2, line 19, insert period after "these".

Col. 2, line 50, change "linolenyl" to --linoleoyl--.

Col. 2, line 51, change "cocyl" to --cocoyl--.

Col. 4, line 57, change "thereof" to --thereto--.

Col. 4, line 59, add title under "Example 1", --Borated Oleoyl Sarcosine--.

Col. 5, line 51, change "axeotropic" to --azeotropic--.

Col. 8, line 30, change "si" to --is--.

Col. 9, line 2, change "mixture" to --mixtures--.

Signed and Sealed this

Twenty-fourth Day of December 1985

[SEAL]

Attest:

DONALD J. QUIGG

Attesting Officer

Commissioner of Patents and Trademarks